United States Patent [19]

Kao et al.

[11] 4,260,814
[45] Apr. 7, 1981

[54] PREPARATION OF ESTERS BY THE THERMAL DECOMPOSITION OF A BIS(2-BROMOALKYL)TELLURIUM DICARBOXYLATE COMPOUND

[75] Inventors: Jar-lin Kao; Ming N. Sheng, both of Cherry Hill, N.J.

[73] Assignee: Atlantic Richfield Company, Los Angeles, Calif.

[21] Appl. No.: 59,729

[22] Filed: Jul. 23, 1979

[51] Int. Cl.³ .............. C07C 67/00; C07C 69/14; C07C 69/24
[52] U.S. Cl. .................. 560/266; 260/550; 560/263; 568/858; 585/641
[58] Field of Search .............. 560/263, 266

[56] References Cited

U.S. PATENT DOCUMENTS 3,668,239  6/1972  Kollar ..................... 560/246

OTHER PUBLICATIONS

Ogawa et al., Bull. Chem. Soc., (Japan), Vol. 41, p. 3031, (1968).

*Primary Examiner*—Vivian Garner
*Attorney, Agent, or Firm*—Delbert E. McCaslin

[57] ABSTRACT

A process for the preparation of bromoalkyl esters and vicinal glycol esters which comprises thermally decomposing at temperatures of from 100° C. to 200° C. a bis(2-bromoalkyl)tellurium dicarboxylate compound of the formula

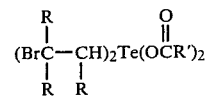

wherein at least one R is hydrogen or R is a methyl group and R' is hydrogen or an alkyl group having 1 to 3 carbon atoms in the presence of an aliphatic monocarboxylic acid selected from formic, acetic, propionic or butyric acid employed as solvent and to facilitate solvolysis in the reaction to give in addition to the bromoalkyl ester, the vicinal glycol ester. An inert acetonitrile solvent may be employed alone to give predominately the bromoalkyl ester or an admixture with the acid may be employed. Oxygen is preferably employed with the carboxylic acid solvent to provide an increase in the mole ratio of vicinal glycol ester to the bromoalkyl ester produced.

5 Claims, No Drawings

PREPARATION OF ESTERS BY THE THERMAL DECOMPOSITION OF A BIS(2-BROMOALKYL)TELLURIUM DICARBOXYLATE COMPOUND

FIELD OF THE INVENTION

The present invention relates to a process for the preparation of bromoalkyl esters and vicinal glycol esters of monocarboxylic acids by the thermal decomposition of a bis(2-bromoalkyl)tellurium 1 to 4 carbon atom carboxylate compound.

BACKGROUND OF THE INVENTION

Numerous prior art processes have been proposed for the preparation of glycol esters of carboxylic acids by reacting an olefinically unsaturated compound such as ethylene and oxygen in the presence of a carboxylic acid and various catalyst systems including tellurium and other variable valent metal compounds together with a halogen source to provide halide ions in solution under oxidation conditions.

Literature articles namely, Kogyo Kagku Zassi, Vol. 73, page 1987 (1970) by M. Ogawa, C. Inone and R. Ishioka; Journ. Prakt. Chem., [4], Vol. 1, page 33 (1954) by H. Funk and Weiss and Angew. Chem. Ind. Ed. Eng. Vol. 10, page 73 (1971) by H. J. Arpe and H. Kuckertz show that tellurium tetrachloride adds across the carbon-carbon double bond in propylene to give substituted organyl tellurium trichloride, and in ethylene and in propylene, when the reagents are mixed in stoichiometric ratio, to give bis(2-haloalkyl)tellurium dichlorides respectively.

In an article by M. Ogawa, Bull. Chem. Soc. Japan, Vol. 41, page 3031 (1968) and the Angew. Chem. Ind. Ed. Eng. Vol. 10, (1971) article noted above there is described the thermal decomposition of bis(2-chloroalkyl)tellurium dichloride which when decomposed gave only olefins, various chloroalkanes, chloroolefins, hydrogen chloride and inorganic tellurium compounds and therefore provided no practical application for the preparation of glycol esters or the respective glycol such as ethylene or propylene glycol.

There is no prior art which describes the thermal decomposition of organic bromoalkyltellurium compounds or the bis(2-bromoalkyl)tellurium carboxylate compounds of the present invention.

Contrary to the prior art teaching and investigative findings, it has surprisingly been discovered that bis(2-bromoalkyl)tellurium dicarboxylate compounds can be thermally decomposed in an aliphatic monocarboxylic acid medium and oxygen to provide excellent yields of vicinal glycol esters such as ethylene glycol diacetate. In addition the reaction may be carried out in an acetonitrile solvent, which is inert to the reaction system, and the absence of oxygen to give a predominent amount of the bromoalkyl ester.

SUMMARY OF THE INVENTION

This invention relates to a process for the preparation of bromoalkyl esters and vicinal glycol esters by the thermal decomposition at a temperature of from about 100° C. to 200° C. a bis(2-bromoalkyl)tellurium dicarboxylate compound in the presence or absence of an aliphatic monocarboxylic acid selected from formic, acetic, propionic, butyric or isobutyric and with or without oxygen, to selectively produce the vicinal glycol esters or bromoalkyl esters respectively.

It is an object of this invention, therefore, to provide a process for the production of bromoalkyl and vicinal glycol esters from bis(2-bromoalkyl)tellurium dicarboxylate compounds at high conversions and selectivities.

It is a further object of this invention to provide a specific process for the preparation of bromoalkyl esters and vicinal glycol esters from specific bis(2-bromo $C_2$ to $C_4$ alkyl)tellurium $C_1$ to $C_4$ dicarboxylate compounds which esters have significant industrial importance as solvents, plasticizers and for the preparation of the respective glycols.

These and other objects and advantages of this invention will become apparent from the description of the invention which follows and from the claims.

DESCRIPTION OF THE INVENTION

In accordance with this invention, 2-bromoalkyl esters and vicinal glycol esters are produced by the thermal decomposition at temperatures of from about 100° C. to 200° C. of a bis(2-bromoalkyl)tellurium dicarboxylate compound having the formula:

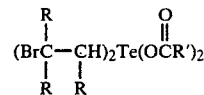

wherein at least one R is hydrogen or R is a methyl group and R' is hydrogen or an alkyl group having from 1 to 3 carbon atoms in the presence of an aliphatic monocarboxylic acid selected from formic, acetic, propionic, butyric or isobutyric as a solvent and to provide solvolysis in the reaction system to give in addition to the 2-bromoalkyl ester, the vicinal glycol ester. Oxygen is preferably employed with the monocarboxylic solvent system to provide an increase in the molar ratio of vicinal glycol ester to the 2-bromoalkyl ester produced. The decomposition reaction may also be carried out in the presence of solely an inert acetonitrile solvent with or without oxygen to provide essentially all 2-bromoalkyl ester. Mixtures of acetonitrile with the monocarboxylic acid solvent-solvolysis system with or without oxygen may also be employed.

The preparation of the 2-bromoalkyl esters and vicinal glycol esters employing an acetic acid (HOAc) solvent medium may be represented by the following unbalanced postulated equation:

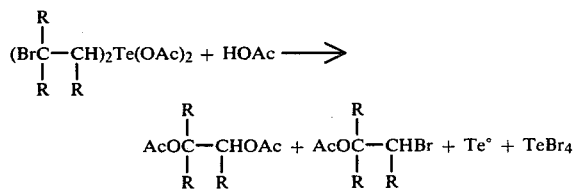

wherein exclusively a 1,2-glycol diacetate and 2-bromoalkyl acetate are produced.

The decomposition reaction may be carried out in any suitable reactor equipped with a gas inlet and outlet and generally with a means for agitation. A general procedure is to charge the bis(2-bromoalkyl)tellurium dicarboxylate and the monocarboxylic acid or acetonitrile solvent or mixtures thereof into the reaction vessel and then heat the mixture to the desired temperature for the appropriate period. The process is preferably carried out under a pressure of oxygen when an acid solvent-solvolysis system is employed to give an increase in the molar ratio of vicinal glycol ester over the 2-bromoalkyl ester produced. The reaction may be carried out as a batch, semi-continuous or continuous process and the addition of materials may be varied to suit the particular apparatus employed. The decomposition products may be recovered by any conventional method such as by distillation, filtration, etc. to effect separation of the desired products from unreacted materials, tellurium, tellurium compounds formed by the reaction, etc.

The bis(2-bromoalkyl)tellurium dicarboxylate compounds which may be employed in the process of the present invention include bis(2-bromoethyl)tellurium diformate, diacetate, dipropionate and dibutanoate as well as the corresponding bis(2-bromopropyl)tellurium and bis(2-bromobutyl)tellurium diformate, diacetate, dipropionate and dibutanoate compounds.

The aliphatic monocarboxylic acids employed in the process of this invention and employed as solvent and to provide solvolysis in the reaction system and thus providing some of the ester moiety to the vicinal glycol esters produced are the lower aliphatic monocarboxylic acids having from 1 to 4 carbon atoms and include formic, acetic, propionic, butyric and isobutyric acids. The monocarboxylic acid may be continuously added to the reaction system as required and may be employed in excess of the amount required to supply the ester moiety in the reaction. Generally a commercial or technical grade of acid, i.e., acids having about 80 weight percent or higher acid concentration are employed although lower concentrations may be used.

Acetonitrile which is inert to the decomposition reaction system may be employed solely as a solvent to provide essentially all 2-bromoalkyl ester reaction product. The absence or presence of oxygen does not materially affect the preparation of the 2-bromoalkyl ester.

The oxygen which is preferably employed along with the aliphatic monocarboxylic acid solvent-solvolysis system to provide an increase in the molar ratio of the vicinal glycol ester to the 2-bromoalkyl ester produced may be in the concentrated form or as an oxygen-containing gas such as air or oxygen diluted with an inert gas such as nitrogen or carbon dioxide, etc. The oxygen pressures employed will generally be between about atmospheric pressure and 100 psig. Higher oxygen pressures may be used but pressures which may form explosive mixtures with the organic compound are to be avoided. Sub-atmospheric pressures may be used but do not appear to provide any process advantage.

The decomposition reaction will proceed at temperatures of from about 100° C. to 200° C. and are preferably maintained at between about 135° C. to 175° C. to obtain the most convenient rate of reaction. Heating and/or cooling means may be employed interior or exterior of the reaction to maintain the temperature within the desired range.

The time of reaction is generally dependent on the bis(2-bromoalkyl)tellurium dicarboxylate compound being reacted, temperature and type of equipment being employed. Generally about one hour is required to obtain the desired conversion and selectivity to the 2-bromoalkyl ester and/or vicinal glycol ester however, shorter or longer reaction times may be employed. Reaction time will vary dependent on whether the process is continuous, semi-continuous or batch.

The Examples which follow are provided to illustrate the invention in accordance with the principles of this invention but are not to be construed as limiting the invention in any way except as indicated by the appended claims.

Preparation of the Bis(2-bromoalkyl)tellurium Dicarboxylate Compounds

In an article by N. Petragnani, J. V. Comasseto and N. H. Varella, Journ. Organometal. Chem., Volume 120, page 375 (1976) there is described a method for preparing di-p-tolyltellurium diacetate via the exchange reaction of di-p-tolyltellurium dichloride with acetic acid on a carboxylate anionic exchange resin, namely (Amberlite IR45 of Rohm and Haas Co., a basic anion exchange resin).

By a modification of the above procedure bis(2-bromoethyl)tellurium diacetate was prepared as follows: A 3.8 percent ethanolic solution of acetic acid was passed through a 15 mm. I.D. glass column charged with 30 g. of a weakly basic anion exchange resin (sold, for example, commercially as "Amberlyst A-21" by Rohm and Haas Co.) and having the following typical properties, a density of 37 to 42 lbs./cu. ft., a particle size (U.S. Standard sieve) of 20 to 50 mesh, a total anion exchange weight capacity of 4.2 milliequivalents/g. dry (minimum), a surface area of from about 30 to 40 $m^2/g$. and an average pore diameter of from about 900 to 1300 Angstrom units determined for dry resin. The resin was washed with ethanol to remove the excess of acetic acid and dried with a stream of nitrogen. A solution of bis(2-bromoethyl)tellurium dibromide (3.0 g.) in 50 ml. of tetrahydrofuran-ethanol (1:1 volume ratio) was passed over the "Amberlyst A-21" resin. The resin was eluted with 300 ml. of tetrahydrofuran-ethanol (1:1 volume ratio). After evaporation of the tetrahydrofuran-ethanol solution, 2.50 g. of bis-(2-bromoethyl)tellurium diacetate was obtained. In a like manner as hereinabove described, bis(2-bromoethyl)tellurium diformate, bis(2-bromoethyl)tellurium dipropionate, bis(2-bromopropyl)tellurium diacetate, bis(2-bromobutyl)tellurium dibutanoate and bis(2-bromobutyl)tellurium diacetate was prepared by employing the corresponding bis(2-bromoalkyl)tellurium dibromide and monocarboxylic acid such as formic, acetic, propionic and butyric.

Preparation of the bis(2-bromoalkyl)tellurium dibromide compounds employed to produce the bis(2-bromoalkyl)tellurium dicarboxylate compounds of the instant invention are fully described in copending application, Ser. No. 059,730, entitled PREPARATION OF ESTERS FROM ORGANIC BROMOALKYL-TELLURIUM COMPOUNDS filed concurrently with this application and incorporated herein by reference.

EXAMPLES 1 and 2

Bis(2-bromoethyl)tellurium diacetate prepared via the exchange reaction of bis(2-bromoethyl)tellurium dibromide with acetic acid on "Amberlyst A-21" of Rohm and Haas Co. as hereinabove described was reacted in a glacial acetic acid medium at a temperature of 135° C. for 1 hour under a pressure of oxygen and nitrogen. The reaction product was analyzed by gas liquid partition chromatography (glpc.). The experimental results giving percent conversion and selectivities as determined by glpc are summarized in Table 1.

TABLE 1

| Example No. | 1 | 2 |
|---|---|---|
| Charge (grams) | | |
| (BrCH$_2$CH$_2$)$_2$Te(OCCH$_3$)$_2$ 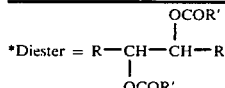 | 0.97 | 1.03 |
| CH$_3$COOH | 4.00 | 4.00 |
| Oxygen (psig) | none | 16 |
| Nitrogen (psig) | 16 | none |
| Mole % Conversion | 64 | 84 |
| Mole % Selectivity to | | |
| Ethylene | trace | trace |
| Ethylene Dibromide | .2 | none |
| 2-bromoethyl acetate | 79 | 24 |
| Ethylene Glycol Diacetate | 19 | 79 |

EXAMPLES 3-5

In Examples 3 to 5 the procedure of Example 2 was repeated employing 1.00 g. of bis(2-bromoethyl)tellurium diacetate, 4.00 g. glacial acetic acid under a 16 psig pressure of oxygen with a variation in reaction temperature and at a reaction time of 1 hour. The conditions and analytical (glpc) results are summarized in Table 2 below.

TABLE 2

| Example No. | 3 | 4 | 5 |
|---|---|---|---|
| Temperature (°C.) | 100 | 150 | 175 |
| Mole % Conversion | 60 | 100 | 100 |
| Mole % Selectivity to | | | |
| Ethylene | 8 | trace | trace |
| 2-bromoethyl Acetate | 60 | 24 | 29 |
| Ethylene Glycol Diacetate | 32 | 76 | 70 |

EXAMPLE 6

The procedure of Example 2 was repeated with the exception that acetonitrile was employed as solvent in the absence of acetic acid. The reaction was carried out at a temperature of 150° C. under a 16 psig pressure of oxygen for 1 hour. Analytical (glpc) results showed a high yield of 2-bromoethyl acetate with a trace of ethylene glycol diacetate and ethylene.

EXAMPLES 7-11

A number of runs were made employing various bis(2-bromoalkyl)tellurium dicarboxylate compounds prepared by the procedure of Example 2 employing an exchange reaction of the bis(2-bromoalkyl)tellurium dibromide with the corresponding aliphatic monocarboxylic acid. The reactions were carried out at a temperature of 150° C. for 1 hour under a 16 psig pressure of oxygen to give the corresponding glycol diester and bromo-ester in high yield. The compounds used and results are set forth in Table 3 below.

TABLE 3

| Ex. No. | Compound | Solvent | Mole % Conversion | Mole % Selectivity to | |
|---|---|---|---|---|---|
| | | | | Diester* | Bromo-ester** |
| 7 | Bis(2-bromoethyl)-tellurium diformate | HCO$_2$H | 85 | 71 | 25 |
| 8 | Bis(2-bromoethyl)-tellurium dipropionate | CH$_3$CH$_2$CO$_2$H | 92 | 79 | 20 |
| 9 | Bis(2-bromopropyl)-tellurium diacetate | CH$_3$CO$_2$H | 95 | 80 | 18 |
| 10 | Bis(2-bromobutyl)-tellurium dibutanoate | CH$_3$(CH$_2$)$_2$CO$_2$H | 88 | 74 | 24 |
| 11 | Bis(2-bromobutyl)-tellurium diacetae | CH$_3$CO$_2$H | 86 | 75 | 22 |

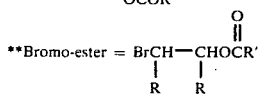

*Diester = R—CH(OCOR')—CH(OCOR')—R

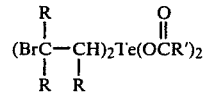

**Bromo-ester = BrCH(R)—CH(R)OCR'(=O)

wherein R and R' are as hereinabove described.

We claim:

1. A process for the preparation of 2-bromoalkyl esters which comprises thermally decomposing at a temperature in the range of from about 100° C. to 200° C. a bis(2-bromoalkyl)tellurium dicarboxylate compound having the formula $$(BrCR_2—CHR)_2Te(OCR'=O)_2$$

wherein R is hydrogen or a methyl group, at least one R being a hydrogen and R' is hydrogen or an alkyl group having 1 to 3 carbon atoms, in the presence of an acetonitrile solvent.

2. A process according to claim 1 wherein the reaction is carried out at a temperature in the range of from about 135° C. to 175° C.

3. A process according to claim 1 wherein the bis(2-bromoalkyl)tellurium dicarboxylate compound is selected from the group consisting of bis(2-bromoethyl)tellurium diformate, bis(2-bromoethyl)tellurium diacetate, bis(2-bromoethyl)tellurium dipropionate, bis(2-bromopropyl)tellurium diacetate, bis(2-bromobutyl)tellurium dibutanoate, and bis(2-bromobutyl)tellurium diacetate.

4. A process according to claim 3 wherein the bis(2-bromoalkyl)tellurium dicarboxylate compound is bis(2-bromoethyl)tellurium diacetate.

5. A process for the preparation of 2-bromoethyl acetate which comprises thermally decomposing at a temperature of from about 135° C. to 175° C. bis(2-bromoethyl)tellurium diacetate in the presence of an acetonitrile solvent.

* * * * *